(12) United States Patent
Hyde et al.

(10) Patent No.: US 8,457,783 B2
(45) Date of Patent: Jun. 4, 2013

(54) COMMUNICATION REGARDING ASPECTS OF A DISPENSED CONSUMABLE COMPOSITION

(75) Inventors: Roderick A. Hyde, Redmond, WA (US); Eric C. Leuthardt, St. Louis, MO (US); Robert W. Lord, Seattle, WA (US); Clarence T. Tegreene, Mercer Island, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 644 days.

(21) Appl. No.: 12/002,794

(22) Filed: Dec. 18, 2007

(65) Prior Publication Data

US 2009/0143899 A1 Jun. 4, 2009

Related U.S. Application Data

(63) Continuation-in-part of application No. 11/998,461, filed on Nov. 29, 2007, and a continuation-in-part of application No. 12/001,061, filed on Dec. 7, 2007, and a continuation-in-part of application No. 12/001,063, filed on Dec. 7, 2007, now Pat. No. 7,804,419.

(51) Int. Cl.
G06F 17/00 (2006.01)

(52) U.S. Cl.
USPC ............. 700/240; 700/236; 700/244

(58) Field of Classification Search
USPC .................... 700/236, 240, 244
See application file for complete search history.

(56) References Cited

U.S. PATENT DOCUMENTS

| 4,223,801 A | 9/1980 | Carlson |
| 4,310,103 A | 1/1982 | Reilly, Jr. et al. |
| 4,641,692 A | 2/1987 | Bennett |
| 4,823,982 A | 4/1989 | Aten et al. |
| 4,899,839 A | 2/1990 | Dessertine et al. |
| RE34,337 E | 8/1993 | Bennett |

(Continued)

OTHER PUBLICATIONS

U.S. Appl. No. 11/998,461, Luethardt, et al.

(Continued)

*Primary Examiner* — Timothy Waggoner
(74) *Attorney, Agent, or Firm* — Suiter Swantz pc llo

(57) ABSTRACT

Methods and systems for programmed dispensation of consumable compositions are provided.
A method for administering a consumable composition may comprise one or more of the following steps: (a) dispensing a dose of a consumable composition according to a programmed dosing schedule; and (b) communicating an aspect of the consumable composition to a system associated with a monitoring entity.
A method for administering a consumable composition may comprise one or more of the following steps: (a) dispensing a dose of a consumable composition according to a programmed dosing schedule; and (b) controlling the functionality of a device according to an aspect of the consumable composition.
A system for administering a consumable composition may comprise one or more of the following: (a) means for dispensing a dose of a consumable composition according to a programmed dosing schedule; and (b) means for communicating an aspect of the consumable composition to a system associated with a monitoring entity.
A system for administering a consumable composition may comprise one or more of the following: (a) means for dispensing a dose of a consumable composition according to a programmed dosing schedule; and (b) means for controlling the functionality of a device according to an aspect of the consumable composition.

24 Claims, 10 Drawing Sheets

U.S. PATENT DOCUMENTS

| | | | |
|---|---|---|---|
| 5,329,459 A | 7/1994 | Kaufman et al. | |
| 5,342,518 A | 8/1994 | Posner et al. | |
| 5,372,276 A | 12/1994 | Daneshvar | |
| 5,408,443 A | 4/1995 | Weinberger | |
| 5,454,406 A | 10/1995 | Rejret et al. | |
| 5,522,525 A | 6/1996 | McLaughlin et al. | |
| 5,651,887 A | 7/1997 | Posner et al. | |
| 5,681,507 A | 10/1997 | Kazuma | |
| 5,752,621 A | 5/1998 | Passamante | |
| 5,850,344 A | 12/1998 | Conkright | |
| 5,851,445 A | 12/1998 | Kazuma | |
| 5,955,009 A | 9/1999 | Kazuma | |
| 5,958,307 A | 9/1999 | Kazuma | |
| 5,971,594 A | 10/1999 | Sahai et al. | |
| 6,054,928 A | 4/2000 | Lemelson et al. | |
| 6,068,156 A | 5/2000 | Liff et al. | |
| 6,113,080 A | 9/2000 | Kazuma | |
| 6,183,691 B1 | 2/2001 | Swank et al. | |
| 6,249,717 B1 * | 6/2001 | Nicholson et al. | 700/241 |
| 6,252,494 B1 * | 6/2001 | Howell | 340/309.8 |
| 6,263,259 B1 | 7/2001 | Bartur | |
| 6,304,797 B1 | 10/2001 | Shusterman | |
| 6,330,957 B1 | 12/2001 | Bell-Greenstreet | |
| 6,332,100 B1 | 12/2001 | Sahai et al. | |
| 6,529,801 B1 | 3/2003 | Rosenblum | |
| 6,539,281 B2 | 3/2003 | Wan et al. | |
| 6,625,518 B2 | 9/2003 | Depeursinge | |
| 6,636,780 B1 | 10/2003 | Haitin et al. | |
| 6,684,920 B2 | 2/2004 | Seitz et al. | |
| 6,697,704 B2 | 2/2004 | Rosenblum | |
| 6,732,884 B2 | 5/2004 | Topliffe et al. | |
| 6,766,218 B2 | 7/2004 | Rosenblum | |
| 6,766,219 B1 * | 7/2004 | Hasey | 700/242 |
| 6,773,668 B1 | 8/2004 | Everson et al. | |
| 6,892,941 B2 | 5/2005 | Rosenblum | |
| 7,072,738 B2 | 7/2006 | Bonney et al. | |
| 7,080,755 B2 * | 7/2006 | Handfield et al. | 700/237 |
| 7,175,081 B2 | 2/2007 | Andreasson et al. | |
| 7,295,890 B2 | 11/2007 | Jean-Pierre | |
| 7,440,818 B2 * | 10/2008 | Handfield et al. | 700/240 |
| 7,444,203 B2 | 10/2008 | Rosenblum | |
| 7,454,267 B2 | 11/2008 | Bonney et al. | |
| 7,469,820 B2 | 12/2008 | Rosenblum | |
| 7,471,993 B2 | 12/2008 | Rosenblum | |
| 7,502,664 B2 * | 3/2009 | Berg | 700/236 |
| 7,516,082 B2 | 4/2009 | Sanville et al. | |
| 7,630,791 B2 | 12/2009 | Nguyen et al. | |
| 7,774,097 B2 | 8/2010 | Rosenblum | |
| 7,831,336 B2 | 11/2010 | Gumpert | |
| 7,844,361 B2 | 11/2010 | Jean-Pierre | |
| 8,019,471 B2 | 9/2011 | Bogash et al. | |
| 8,195,330 B2 | 6/2012 | Coe | |
| 8,325,011 B2 | 12/2012 | Butler et al. | |
| 2001/0011501 A1 | 8/2001 | Sato et al. | |
| 2001/0045242 A1 | 11/2001 | Clusserath et al. | |
| 2002/0088817 A1 | 7/2002 | Bell-Greenstreet | |
| 2003/0050731 A1 | 3/2003 | Rosenblum | |
| 2003/0084957 A1 | 5/2003 | Seitz et al. | |
| 2003/0088332 A1 | 5/2003 | Rosenblum | |
| 2003/0093181 A1 | 5/2003 | Rosenblum | |
| 2004/0164146 A1 | 8/2004 | Rosenblum | |
| 2004/0215369 A1 | 10/2004 | Rosenblum | |
| 2004/0249250 A1 | 12/2004 | McGee et al. | |
| 2005/0065645 A1 | 3/2005 | Liff et al. | |
| 2006/0097000 A1 | 5/2006 | Gumpert | |
| 2006/0259195 A1 | 11/2006 | Eliuk et al. | |
| 2006/0266763 A1 | 11/2006 | Svabo Bech | |
| 2006/0283876 A1 | 12/2006 | Mocnik et al. | |
| 2007/0145067 A1 | 6/2007 | Headlee | |
| 2007/0184219 A1 | 8/2007 | Johnson | |
| 2007/0293982 A1 | 12/2007 | Rosenblum | |
| 2008/0173705 A1 | 7/2008 | Girard et al. | |
| 2008/0195251 A1 | 8/2008 | Milner | |
| 2008/0283542 A1 | 11/2008 | Lanka et al. | |
| 2009/0048712 A1 | 2/2009 | Rosenblum | |
| 2009/0057341 A1 | 3/2009 | Girard et al. | |
| 2009/0134181 A1 | 5/2009 | Wachman et al. | |
| 2010/0324728 A1 | 12/2010 | Rosenblum | |

OTHER PUBLICATIONS

U.S. Appl. No. 12/001,061, Hyde, et al.
U.S. Appl. No. 12/001,063, Hyde, et al.
U.S. Appl. No. 12/004,094, Hyde, et al.
U.S. Appl. No. 12/006,252, Hyde, et al.
U.S. Appl. No. 12/012,500, Hyde, et al.
U.S. Appl. No. 12/074,245, Hyde, et al.
U.S. Appl. No. 12/927,038, Hyde, et al.

* cited by examiner

COMMUNICATION REGARDING ASPECTS OF A DISPENSED CONSUMABLE COMPOSITION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of United States Patent Application having U.S. patent application Ser. No. 11/998,461, entitled Programmed Dispensing of Consumable Compositions, naming Eric Leuthardt, Casey Tegreene, Lowell Wood, Rod Hyde and Bob Lord as inventors, filed Nov. 29, 2007, which is currently co-pending, or is an application of which a currently co-pending application is entitled to the benefit of the filing date.

For purposes of the USPTO extra-statutory requirements, the present application constitutes a continuation-in-part of United States Patent Application having U.S. patent application Ser. No. 12/001,061, entitled Programmed Dispensing of Consumable Compositions, naming Eric Leuthardt, Casey Tegreene, Lowell Wood, Rod Hyde and Bob Lord as inventors, filed Dec. 7, 2007, which is currently co-pending, or is an application of which a currently co-pending application is entitled to the benefit of the filing date.

For purposes of the USPTO extra-statutory requirements, the present application constitutes a continuation-in-part of United States Patent Application having U.S. patent application Ser. No. 12/001,063, entitled Programmed Dispensing of Consumable Compositions, naming Eric Leuthardt, Casey Tegreene, Lowell Wood, Rod Hyde and Bob Lord as inventors, filed Dec. 7, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

Figure 1:
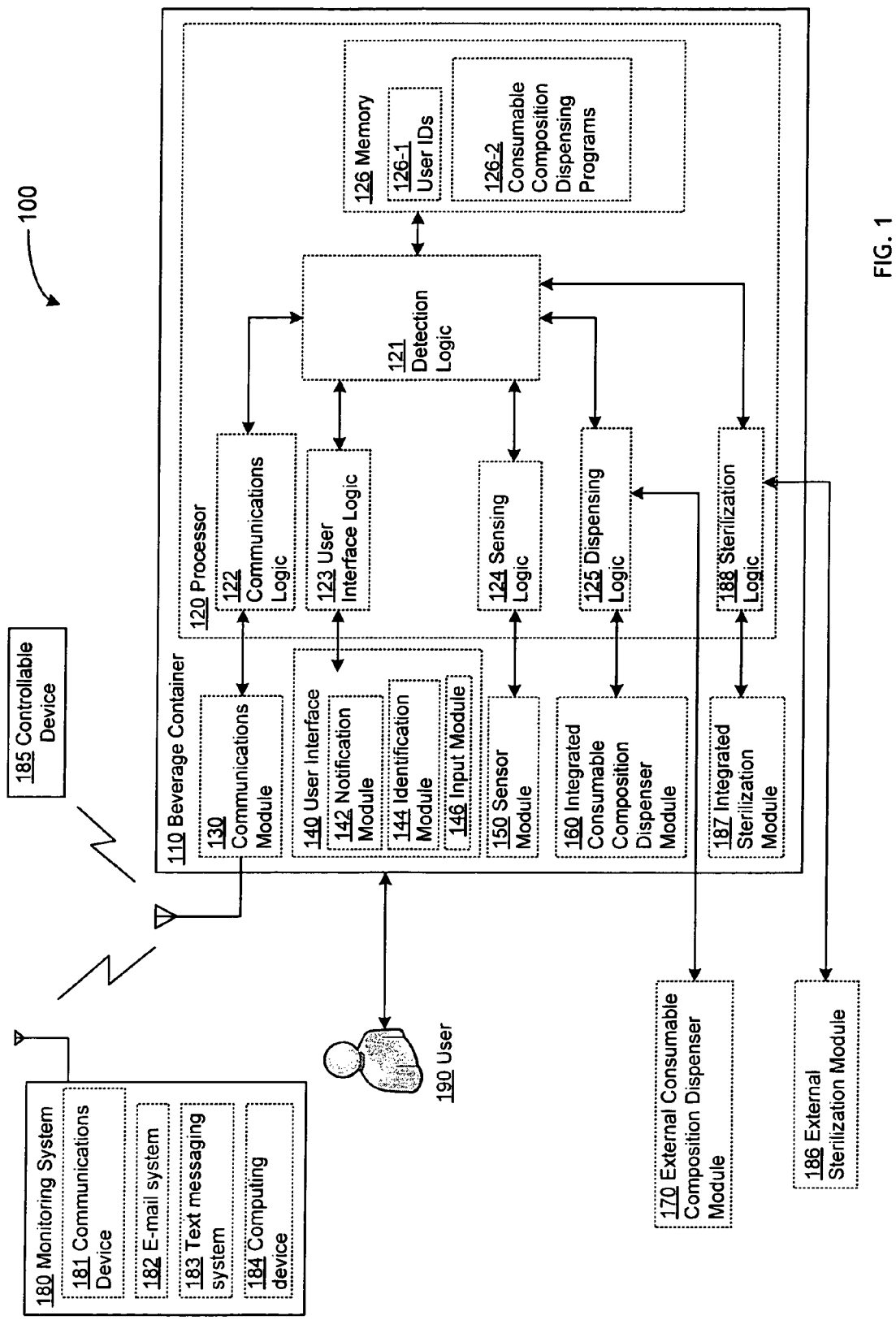
FIG. 1 shows a high-level block diagram of a beverage container.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more technologies may be implemented. A consumable composition dispensing system 100 may comprise a beverage container 110 to be used by user 190. The beverage container 110 may include any receptacle configured for retaining a liquid or gel composition. For example, the beverage container 110 may include a cup, glass, mug, bowl, pitcher, jug, or the like.

The beverage container 110 may include a processor 120, a communications module 130, a user interface 140, a sensor module 150, an integrated consumable composition dispenser module 160, and/or an integrated sterilization module 187.

Processor 120 may include communications logic 122, user interface logic 123, sensing logic 124, dispensing logic 125, memory 126, and/or sterilization logic 188.

Memory 126 may include user IDs 126-1 and/or consumable composition dispensing programs 126-2.

User interface 140 may include a notification module 142, an identification module 144, and/or an input module 146.

Sensor module 150 may include one or more of a light source sensor, a position sensor, an emission sensor, a spectrophotometer, an infrared or ultraviolet sensor, a biometric sensor and the like. Sensor module 150 may include a biometric sensor which senses the presence of saliva, perspiration, sebum and the like, either on the surface of the beverage container 110 or as a component of the contents therein. Sensor module 150 may include an accelerometer, an inertial motion sensor, and the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110. Sensor module 150 may include a capacitive concentration sensor which may sense a concentration of the consumable composition present in the beverage container 110. Sensor module 150 may include an inclinometer and the like. Sensor module 150 may include a flowmeter for sensing a flowrate into or out of the beverage container 110. Sensor module 150 may include a capacitive level sensor, such as a strip or—dual-probe sensor (e.g., a strip running down that side of the cup to sense a fluid level based at least in part between differences in the known/inferred/assumed dielectric constants of air and a fluid). In some instances, the dielectric constant is recalled/calculated in response to a sensed composition of a fluid (e.g., sensed constituents of an alcoholic cocktail); in other instances, the dielectric constant is assumed (e.g., defaults to that of water); in yet other instances, The consumable composition dispensing system 100 may further include an external consumable composition dispenser module 170 and/or external sterilization module 186.

Figure 2:
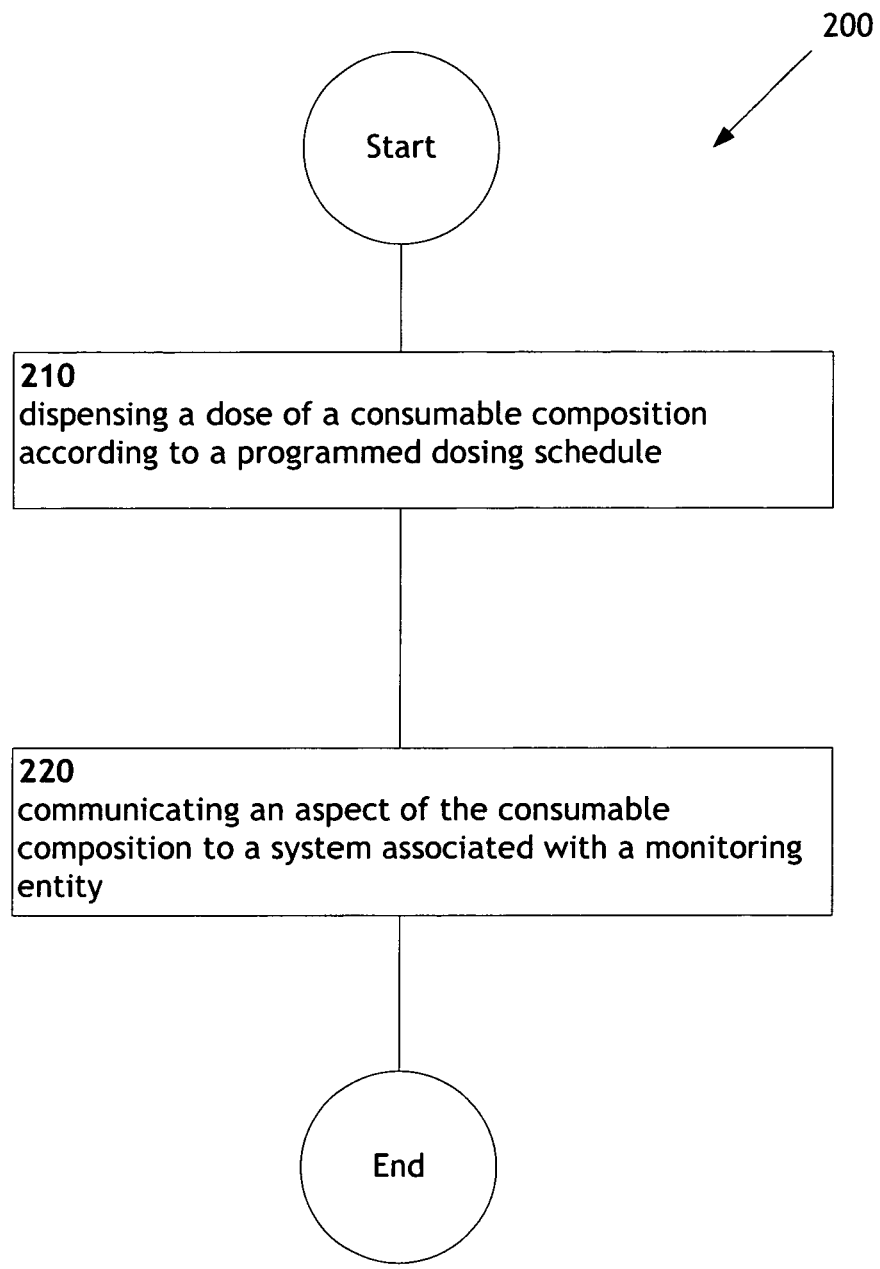
FIG. 2 is a high-level logic flowchart of a process.

FIG. 2 illustrates an operational flow 200 representing example operations related to programmed dispensing of consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to a dispensing operation 210, where dispensing a dose of a consumable composition according to a programmed dosing schedule may occur (e.g. distributing a pharmaceutical composition in accordance with a user or physician-defined regimen). For example, as shown in FIG. 1, integrated consumable composition dispenser module 160, and/or external consumable composition dispenser module 170 may distribute doses (e.g. 30 mg) of a consumable composition (e.g. an anti-depressant, such as Paroxotene) into a beverage container 110 (e.g. a cup).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosponates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, or the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., dimethylaminoethanol (DMAE), dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea), or the like.

Then, in a communicating operation 220, communicating an aspect of the consumable composition to a system associated with a monitoring entity may occur (e.g. a user's failure to ingest an amount of a pharmaceutical composition may be communicated to a physician). For example, as shown in FIG. 1, the communications module 130 may transmit data regarding an aspect of the consumable composition (e.g. an amount of the consumable composition dispensed) to an outside entity such as a monitoring system 180 (e.g. a hospital computer network) or a controllable device 185 (e.g. a cell phone). The transmission may be via wireless (e.g. Bluetooth®, WiFi, cellular, satilite, RF, IR and the like) and/or hard line (e.g. phone line) connections. The transmissions may be encrypted or otherwise protected so as to ensure privacy regarding the contents of the communicated information.

The aspect of the consumable composition may include, but is not limited to, an amount of consumable composition dispensed into the beverage container 110, an amount of consumable composition present in the beverage container 110, an amount of the composition removed from the beverage container 110, an identity of the consumable composition, an identity of a user 190, a user input, a programmed schedule for dispensing the consumable composition, or the like.

Monitoring system 180 may also transmit a notification (e.g. a notification that a programmed dosing schedule has been transmitted to the system 100) to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM), and/or a computing device 184 (e.g. a personal digital assistant (PDA), personal computer, laptop, music player and/or gaming device).

Figure 3:
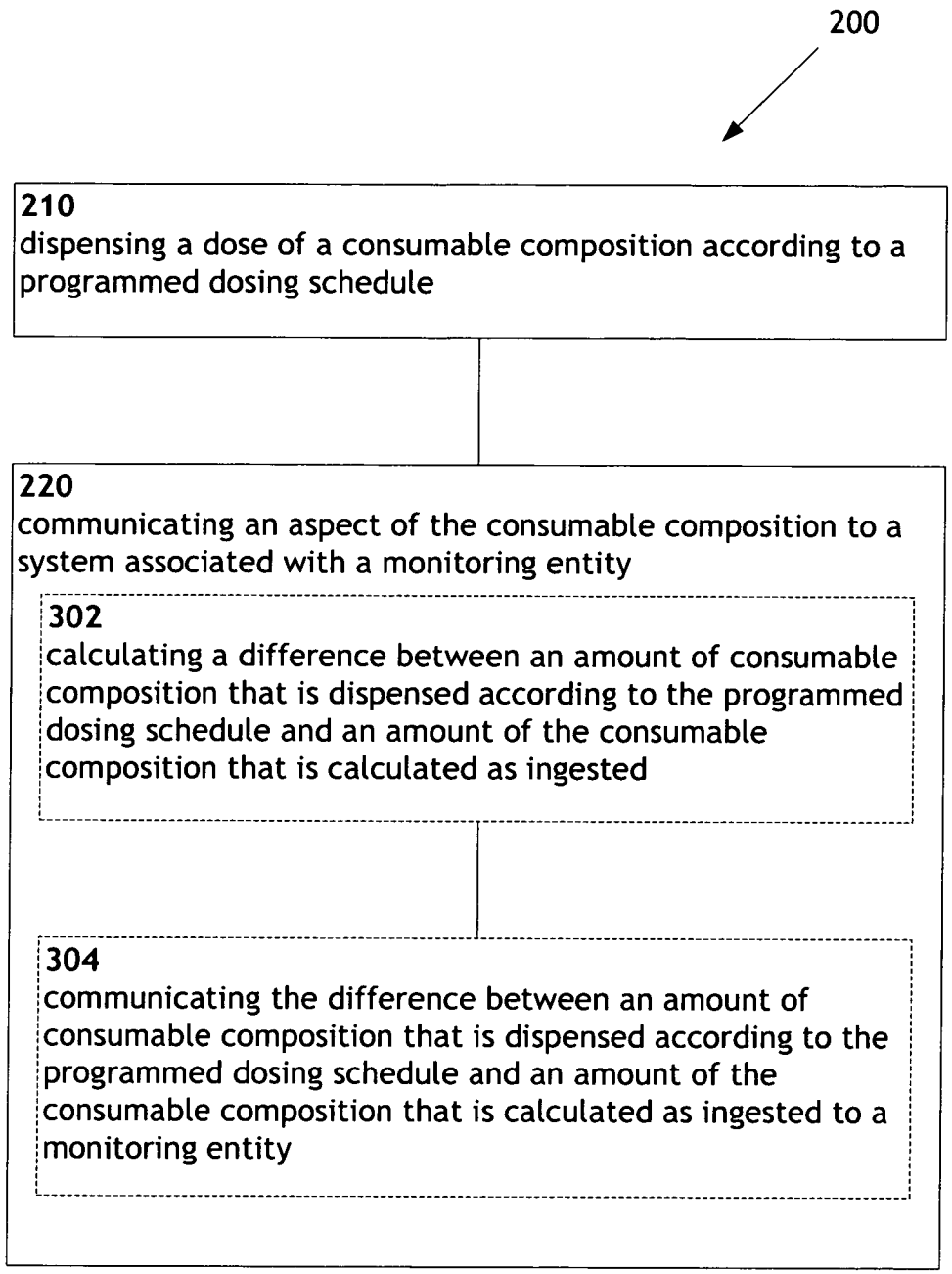
FIG. 3 is a high-level logic flowchart of a process depicting alternate implementations of FIG. 2.

FIG. 3 illustrates alternative embodiments of the example operational flow 200 of FIG. 2. FIG. 3 illustrates example embodiments where the communicating operation 220 may include at least one additional operation. Additional operations may include an operation 302, and/or an operation 304 At the operation 302, calculating a difference between an amount of the consumable composition that is dispensed according to the programmed dosing schedule and an amount of the consumable composition that is calculated as ingested may occur (e.g. 60 mg dispensed–40 mg calculated as ingested=20 mg not ingested). For example, as shown in FIG. 1, sensor module 150 may include an inclinometer which may measure a degree of inclination of the beverage container 110 with respect to the resting postion of the beverage container 110. A movement which maintains the beverage container in a position rotated at least 90° (e.g. 110°) from its resting position for a given period of time (e.g. 15 seconds) may indicate ingestion of some or all of the contents of the beverage container. The period of time may be a function of the degree of rotation and the flow characteristics of the contents of the beverage container.

Further, sensor module 150 may include a capacitve level sensor (e.g. a capacitive strip sensor) which may detect a level of fluid in the beverage container 110. A change in the resting-position fluid level in a beverage container 110 over a given period of time (e.g. level drops 3 inches in 10 seconds) may indicate ingestion of some or all of the contents of the beverage container.

The sensing logic 124 may provide data regarding ingestion of the consumable composition obtained from the sensor module 150 to the detection logic 121. The detection logic 121 may calculate an amount of consumable composition that may have been ingested. The dispensing logic 125 may provide the amount of consumable composition either previously dispensed by or currently remaining in the integrated consumable composition dispenser module 160 and/or the external consumable composition dispenser module 170 to the detection logic 121. The detection logic 121 may compare the amount calculated to have been ingested to the amount dispensed or remaining to be dispensed so as to verify user 190 compliance with a programmed dosing schedule.

Further, at the operation 304, communicating the difference between an amount of the consumable composition that is dispensed according to the programmed dosing schedule and an amount of the consumable composition that is calculated as ingested to a monitoring entity may occur (e.g. 20 mg not ingested). For example, as shown in FIG. 1, the communications module 130 may transmit a notification to a monitoring system 180 when an amount of consumable composition calculated as ingested does not correspond to an amount dispensed, thereby indicating non-compliance with a programmed dosing schedule.

Figure 4:
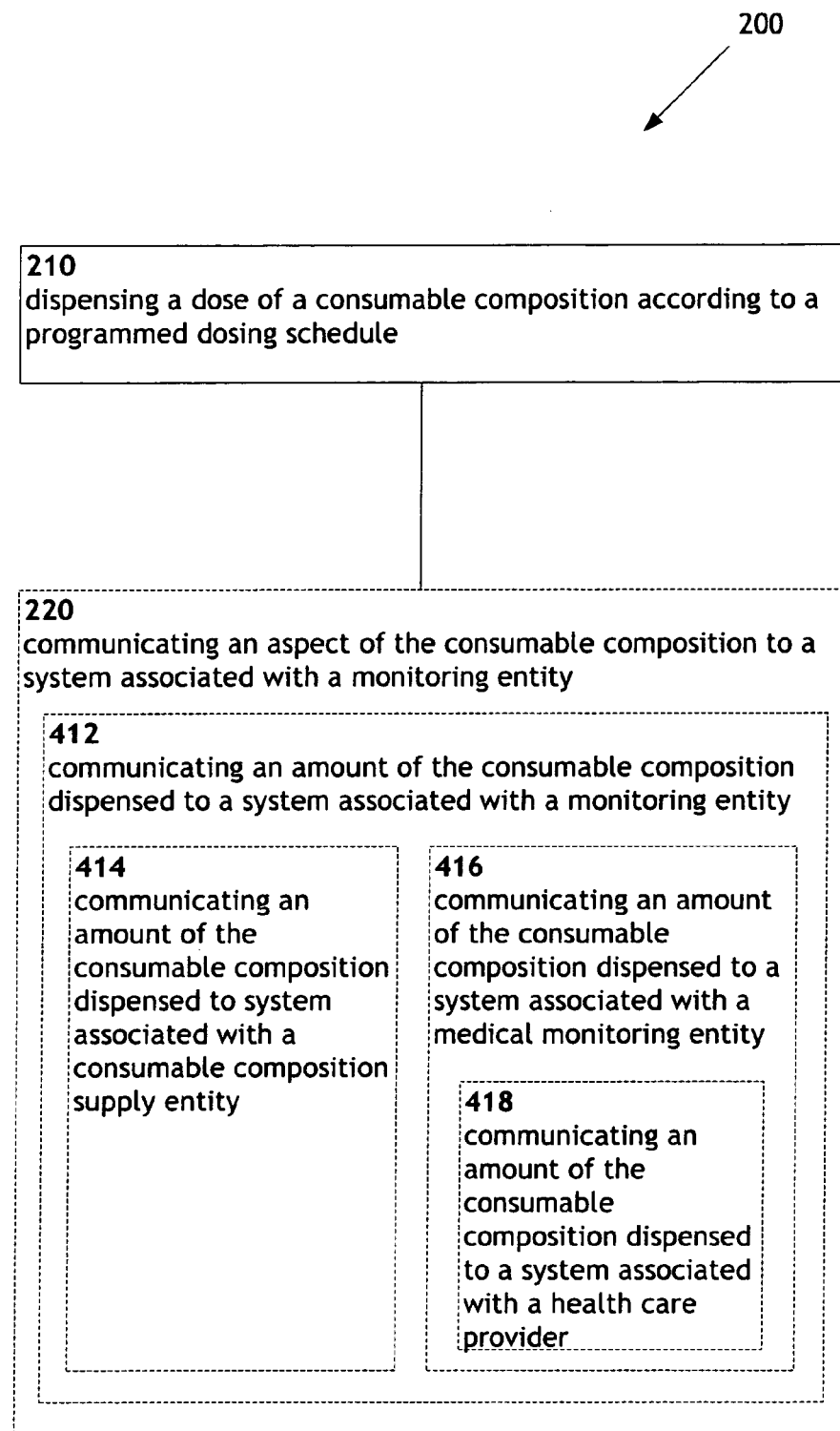
FIG. 4 is a high-level logic flowchart of a process depicting alternate implementations of FIG. 2.

FIG. 4 illustrates alternative embodiments of the example operational flow 200 of FIG. 2. FIG. 4 illustrates example embodiments where the communicating operation 220 may include at least one additional operation. Additional operations may include an operation 412, an operation 414, an operation 416, and/or an operation 418.

At the operation 412, communicating an amount of the consumable composition dispensed to a system associated with a monitoring entity may occur (e.g. notification to an attendant at an assisted living facility that 30 mg of antibiotic have been dispensed to a resident). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180. Further, at the operation 414, communicating an amount of the consumable composition dispensed to a system associated with a consumable composition supply entity (e.g. notification to an online ordering system for a pharmaceutical supply company that a supply of Vicodin has been exhausted). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 associated with a consumable supply entity.

Further, at the operation 416, communicating an amount of the consumable composition dispensed to a system associated with a medical monitoring entity may occur (e.g. notification to and emergency first responder such as a paramedic, firefighter, or police officer that an overdose of a painkiller has been dispensed). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 associated with a medical monitoring entity.

Further, at the operation 418, communicating an amount of the consumable composition dispensed to a system associated with a health care provider may occur (e.g. notification to a local area network (LAN) of a physician's clinic that a prescribed amount of an analagesic has been dispensed). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 associated with a physician.

Figure 5:
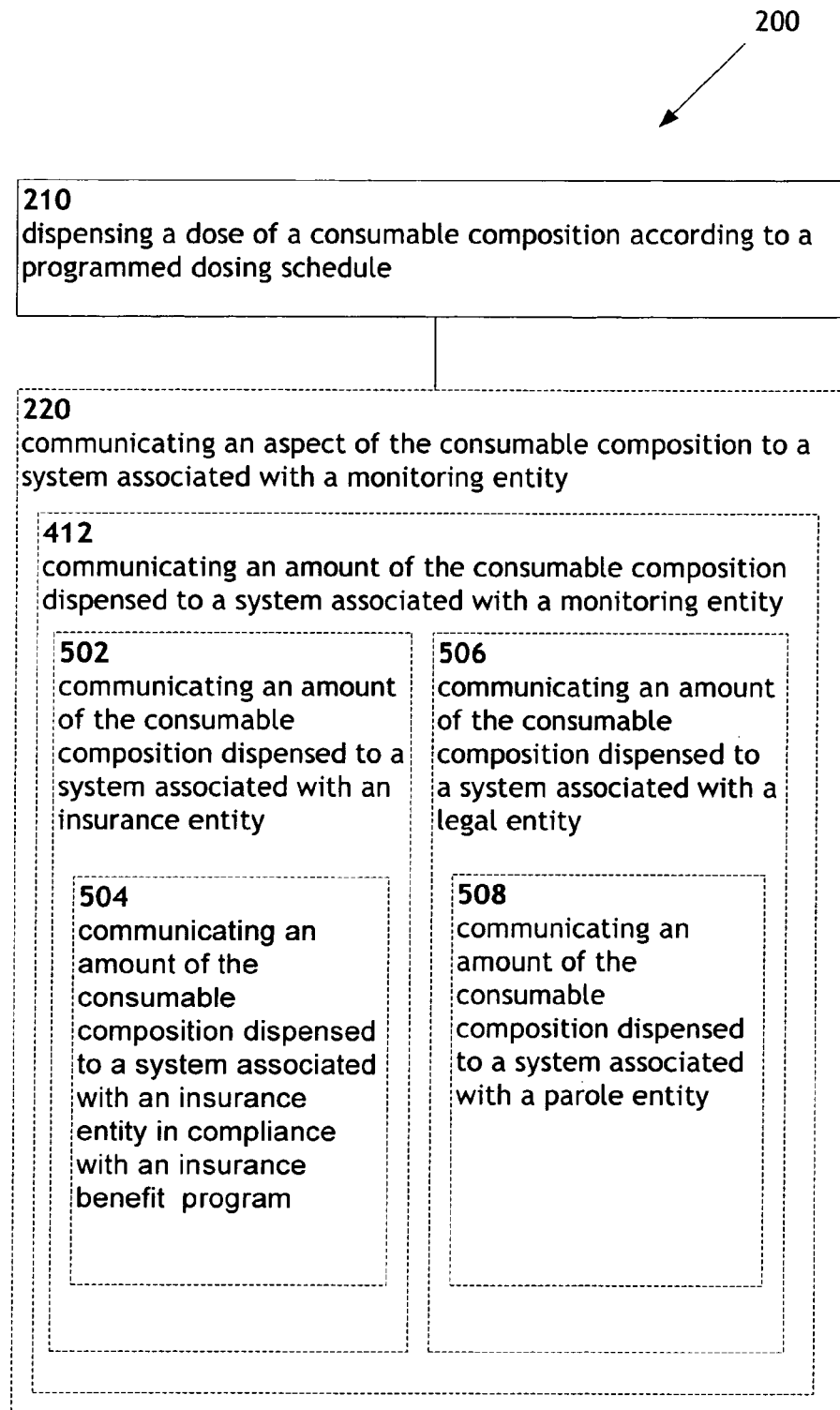
FIG. 5 is a high-level logic flowchart of a process depicting alternate implementations of FIG. 2.

FIG. 5 illustrates alternative embodiments of the example operational flow 200 of FIG. 2. FIG. 5 illustrates example embodiments where the communicating operation 412 may include at least one additional operation. Additional operations may include an operation 502, an operation 504, an operation 506 and/or an operation 508.

At the operation 502, communicating an amount of the consumable composition dispensed to a system associated with an insurance entity may occur (e.g. notification to a LAN of an insurance underwriting company that an insured's health risks are being minimized by dispensing medications as prescribed). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 with an insurance entity.

At the operation 504, communicating an amount of the consumable composition dispensed to a system associated with an insurance entity in compliance with an insurance benefit program may occur (e.g. a reduced health insurance premium rate may be provided when a consistent record of dispensing a consumable composition is communicated to an insurance company). For example, as shown in FIG. 1, the communications logic 122 may cause the communications module 130 may transmit data regarding an aspect of the consumable composition (e.g. dispensation of the consumable composition by the integrated consumable composition dispenser module 160) to a monitoring system 180 associated with an insurance entity. The insurance entity may then provide an insurance benefit (e.g. an insurance premium discount or credit; additional coverage for an additional insured) to the user.

Further, at the operation 506, communicating an amount of the consumable composition dispensed to a system associated with a legal entity may occur (e.g. a notification to a court clerk monitoring compliance with a court order). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 associated with a legal entity.

Further, at the operation 508, communicating an amount of the consumable composition dispensed to a system associated with a parole entity may occur (e.g. a notification to a parole officer regarding compliance with a drug regimen as a condition of parole). For example, as shown in FIG. 1, communications logic 122 may cause communications module 130 to transmit data regarding an amount of a consumable composition dispensed by integrated consumable composition dispenser module 160 and/or external consumable composition dispenser module 170 to a monitoring system 180 associated with a parole entity.

Figure 6:
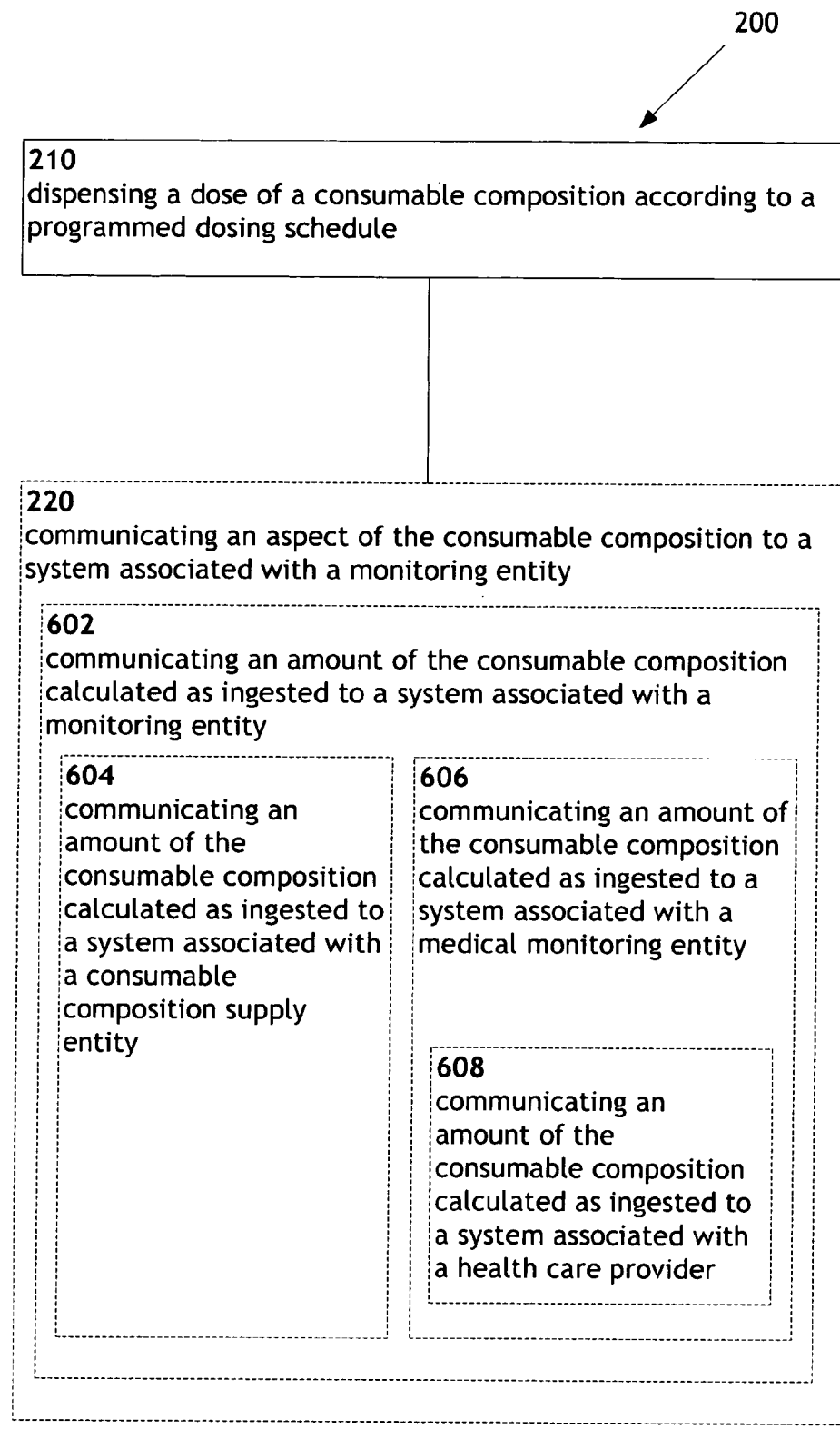
FIG. 6 is a high-level logic flowchart of a process depicting alternate implementations of FIG. 2.

FIG. 6 illustrates alternative embodiments of the example operational flow 200 of FIG. 2. FIG. 6 illustrates example embodiments where the communicating operation 220 may include at least one additional operation. Additional operations may include an operation 602, an operation 604, an operation 606, and/or an operation 608.

At the operation 602, communicating an amount of the consumable composition calculated as ingested to a system associated with a monitoring entity may occur (e.g. notification to a parent that a child has ingested 10 mg of a multivitamin). For example, as shown in FIG. 1, communications logic 122 may cause communications module 130 to transmit data regarding the amount of a consumable composition calculated as ingested by the sensor module 150 to a monitoring system 180. The sensing logic 124 may be operably coupled to a sensor module 150 and may provide sensor data to detection logic 121. Sensor module 150 may include a biometric sensor which senses the presence of saliva, perspiration, sebum and the like, either on the surface of the beverage container 110 or as a component of the contents therein. Sensor module 150 may include an accelerometer, an inertial motion sensor, and the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110. Sensor module 150 may include a capacitive concentration sensor which may sense a concentration of the consumable composition present in the beverage container 110. Sensor module 150 may include an inclinometer which may sense a degree of inclination of the beverage container with respect to its resting position.

Further, at the operation 604, communicating an amount of the consumable composition calculated as ingested to a system associated with a consumable composition supply entity may occur (e.g., notification to an online ordering system for a pharmaceutical supply company that a supply of Percocet has been calculated as ingested). For example, as shown in FIG. 1, communications logic 122 may cause communications module 130 to transmit data regarding an amount of consumable composition calculated as ingested to a monitoring system 180 associated with a consumable composition supply entity.

Further, at the operation 606, communicating an amount of the consumable composition calculated as ingested to a system associated with a medical monitoring entity may occur (e.g. notification to a nurses station that a overdose of an ACE inhibitor has been calculated as ingested). For example, as shown in FIG. 1, communications logic 122 may cause communications module 130 to transmit data regarding an amount of consumable composition calculated as ingested to a monitoring system 180 associated with a medical monitoring entity.

Further, at the operation 608, communicating an amount of the consumable composition calculated as ingested to a system associated with a health care provider may occur (e.g. notification to LAN of a physician's clinic that a prescribed amount of an antipsychotic drug has been calculated as ingested). For example, as shown in FIG. 1, communications logic 122 may cause communications module 130 to transmit data regarding an amount of consumable composition calculated as ingested to a monitoring system 180 associated with a physician.

Figure 7:
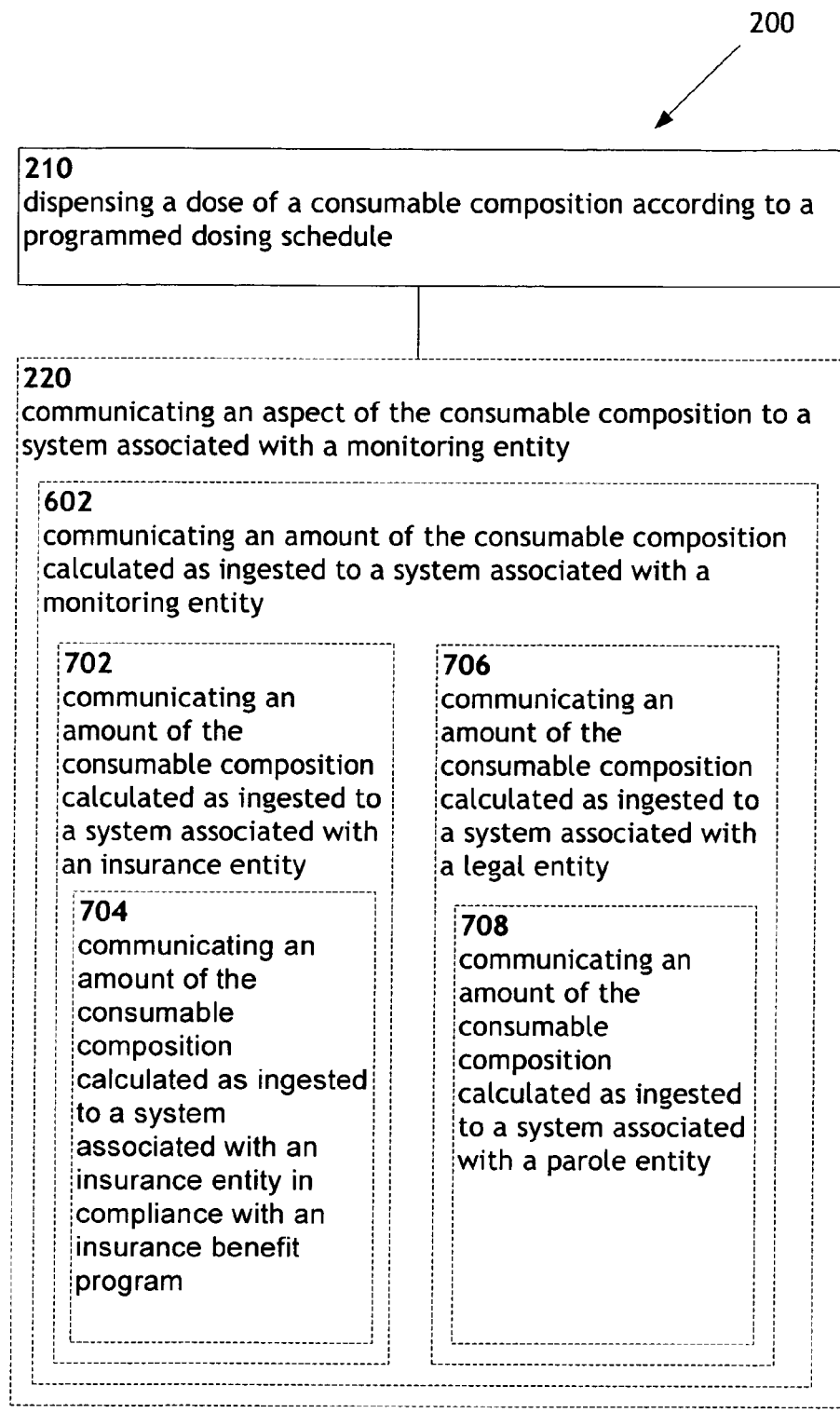
FIG. 7 is a high-level logic flowchart of a process depicting alternate implementations of FIG. 2.

FIG. 7 illustrates alternative embodiments of the example operational flow 200 of FIG. 6. FIG. 2 7 illustrates example embodiments where the communicating operation 602 may include at least one additional operation. Additional operations may include an operation 702, an operation 704, and/or an operation 706.

At the operation 702, communicating an amount of the consumable composition calculated as ingested to a system associated with an insurance entity may occur (e.g. notification to a LAN of an insurance underwriting company that an insured's health risks are being minimized by doses of medications which are calculated as ingested). For example, as shown in FIG. 1, communications logic 122 may cause communications module 130 to transmit data regarding an amount of consumable composition calculated as ingested to a monitoring system 180 associated with an insurance entity.

At the operation 704, communicating an amount of the consumable composition calculated as ingested to a system associated with an insurance entity in compliance with an insurance benefit program may occur (e.g. a credit towards a health insurance premium may be provided when a consistent record of user's ingestion of a consumable composition is communicated to an insurance company). For example, as shown in FIG. 1, the communications logic 122 may cause the communications module 130 may transmit data regarding an aspect of the consumable composition (e.g. dispensation of the consumable composition by the integrated consumable composition dispenser module 170) to a monitoring system 180 associated with an insurance entity. The insurance entity may then provide an insurance benefit (e.g. an insurance premium discount or credit; additional coverage for an additional insured) to the user.

Further, at the operation 706, communicating an amount of the consumable composition calculated as ingested to a system associated with a legal entity may occur (e.g. notification to a parent monitoring ingestion of daily vitamins by a minor). For example, as shown in FIG. 1, communications logic 122 may cause communications module 130 to transmit data regarding an amount of consumable composition calculated as ingested to a monitoring system 180 associated with a legal entity.

Further, at the operation 708, communicating an amount of the consumable composition calculated as ingested to a system associated with a parole entity may occur (e.g. notification to an employer providing employment as a condition of parole of a calculated ingestion of an antidepressant). For example, as shown in FIG. 1, communications logic 122 may cause communications module 130 to transmit data regarding an amount of consumable composition calculated as ingested to a monitoring system 180 associated with a parole entity.

Figure 8:
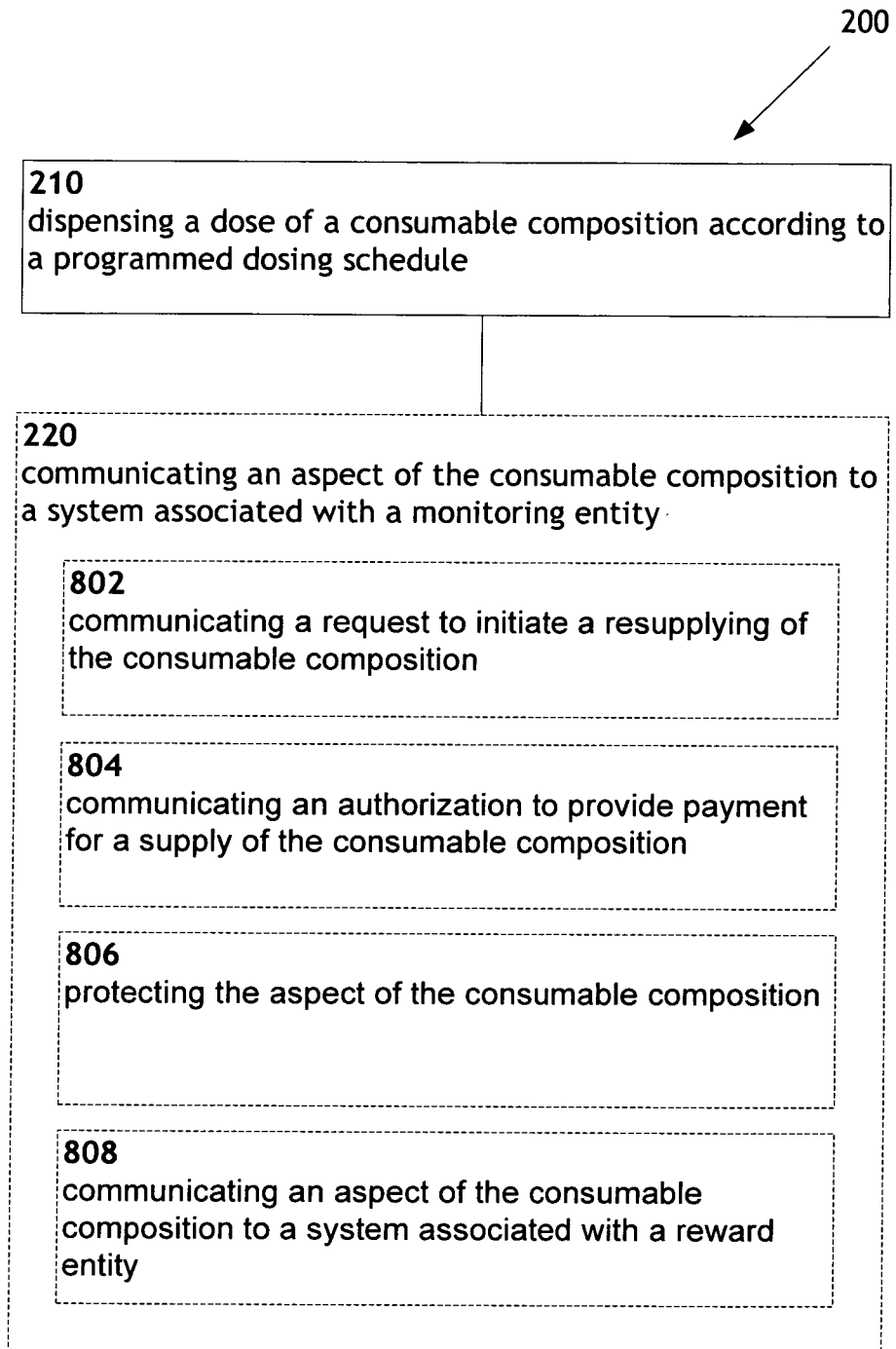
FIG. 8 a high-level logic flowchart of a process depicting alternate implementations of FIG. 2.
Figure 10:
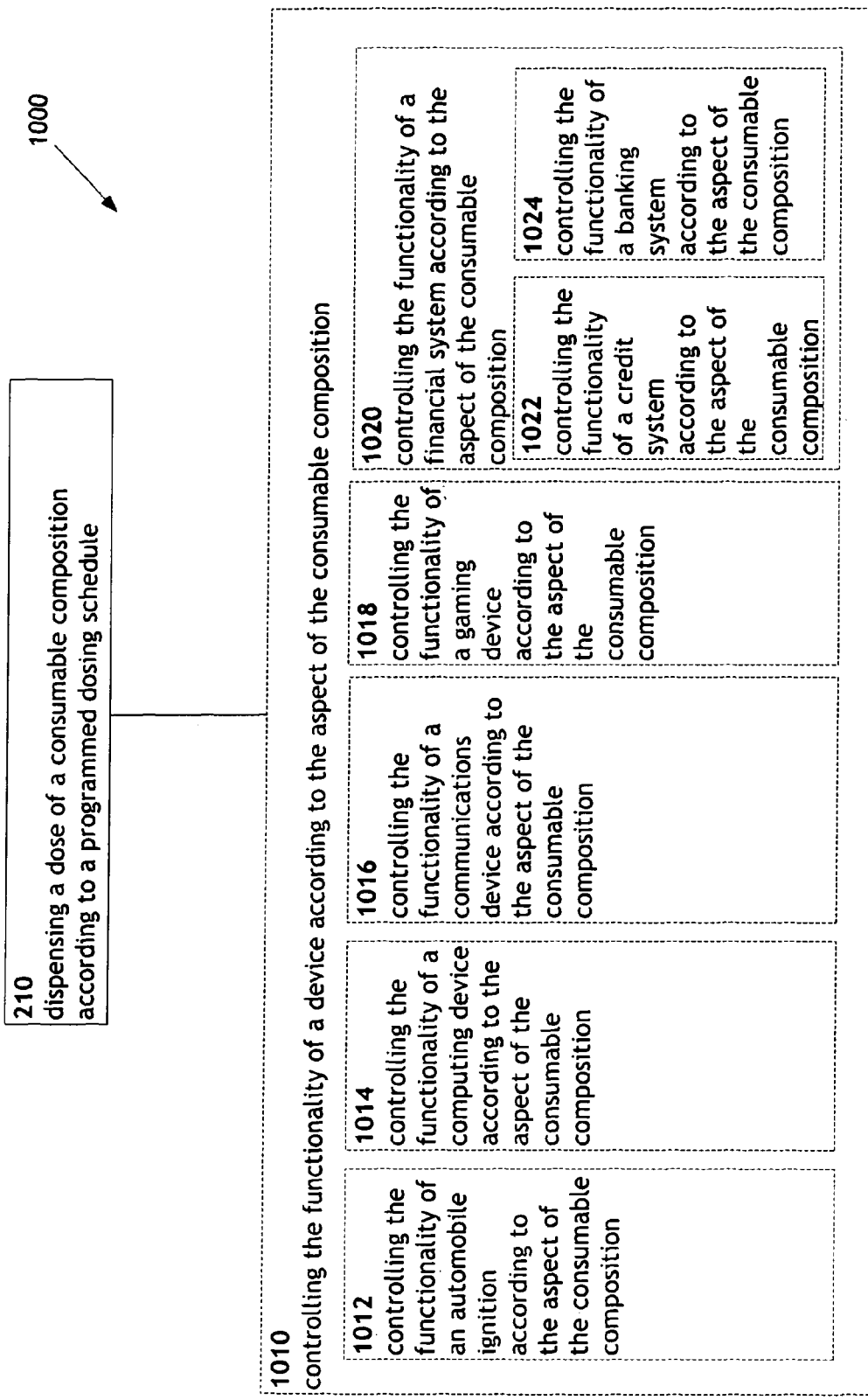
FIG. 10 is a high-level logic flowchart of a process.

FIG. 8 illustrates an operational flow 800 representing example operations related to programmed dispensing of consumable compositions. FIG. 10 illustrates an example embodiment where the example operational flow 200 of FIG. 2 may include at least one additional operation. Additional operations may include an operation 802, 804, 806 and/or an operation 808.

At the operation 802, communicating a request to initiate a resupplying of the consumable composition may occur (e.g. transmitting an order for an additional supply of vitamins to an online supply company via the internet). For example, as shown in FIG. 1, communications logic 122 may cause communications module 130 to transmit data regarding a resupply request when the detection logic 121 has determined that a threshold amount of consumable composition remains in the external consumable composition dispensing module 170.

Further, at the operation 804, communicating an authorization to provide payment for a supply of the consumable composition may occur (e.g. transmitting a request to a bank to issue a check). For example, as shown in FIG. 1, communications logic 122 may cause communications module 130 to transmit data regarding a payment authorization when the detection logic 121 has determined that a resupply request has been issued by the communications module 130.

Further, at the operation 806, protecting the aspect of the consumable composition may occur (e.g. password protecting the data representing an amount of the consumable composition that a user has ingested). For example, as shown in FIG. 1, communications logic 122 may cause communications module 130 to transmit data protected (e.g. access to the data is restricted by a password or passcode, encryption or the like) data regarding an aspect of the consumable composition such that only authorized users of a monitoring system 180 may access the data.

Further, at the operation 808, communicating an aspect of the consumable composition to a system associated with a reward entity may occur (e.g. an authorization to issue monetary reward is transmitted upon verification of an ingestion of an anti-depressant). For example, as shown in FIG. 1, communications logic 122 may cause communications module 130 to transmit data (e.g. authorization data, compliance data, consumable composition aspect data) regarding compliance with a programmed dosing schedule for a consumable composition to a monitoring system 185 associated with a reward entity. A reward entity may include an entity providing incentives (e.g. cash rewards, airline mileage rewards, prize rewards) for user 190 compliance with a programmed dosing schedule for a consumable composition.

Figure 9:
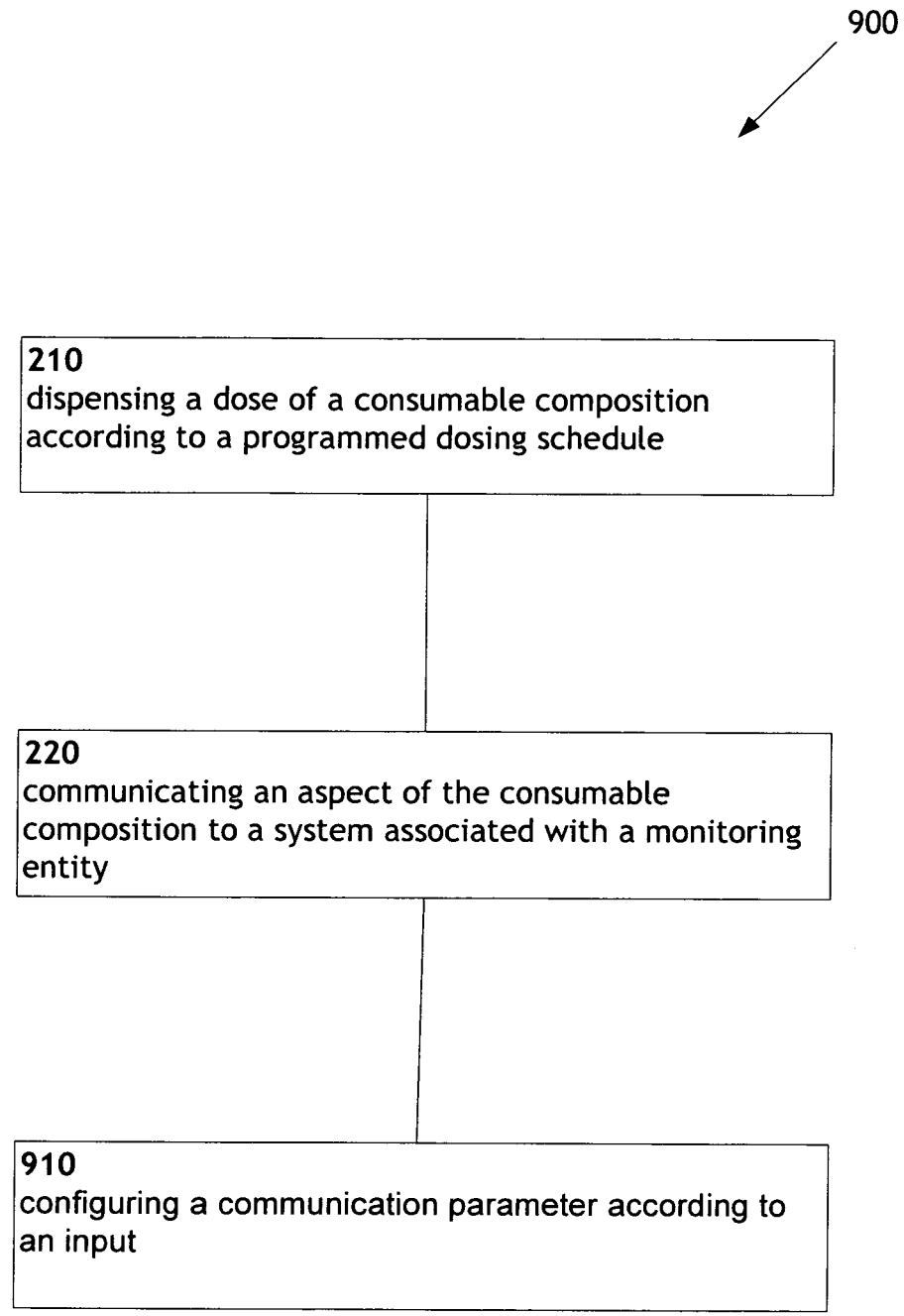
FIG. 9 is a high-level logic flowchart of a process.

FIG. 9 illustrates an operational flow 900 representing example operations related to programmed dispensing of consumable compositions. After a start operation, a dispensing operation 210, and a communication operation 220, the operational flow 900 moves to a configuring operation 910 where configuring a communication parameter according to an input may occur (e.g. a time interval at which an amount of the consumable composition dispensed is communicated to a monitoring entity is specified). For example, an input specifying a communication parameter may be receive via the input module 146 of the user interface 140 (e.g. keyboard commands) or from an outside monitoring system 180 via the communications module 130 (e.g. RF signals). The communication parameter may include timing of notifications to be communicated, parties to which communications are to be directed (or not directed), communication mechanisms to utilize (e.g. text message, e-mail, phone call) and the like.

FIG. 10 illustrates an operational flow 1000 representing example operations related to programmed dispensing of consumable compositions. After a start operation, and a dispensing operation 210, the operational flow 1000 moves to a controlling operation 1010, where controlling the functionality of a device according to an aspect of the consumable composition may occur (e.g. controlling the functionality of an automobile ignition according to an amount of consumable composition ingested). For example, as shown in FIG. 1, communications logic 122 may cause communications module 130 to transmit control data to a controllable device 185 according to an aspect of the consumable composition.

At the operation 1012, controlling the functionality of an automobile according to the aspect of the consumable composition may occur (e.g. automobile will not start unless an amount of the consumable composition has been calculated as ingested). For example, as shown in FIG. 1, control logic 122 may cause communications module 130 to transmit control data (e.g., an ignition code) to a controllable device, such as an automobile, according to the aspect of the consumable composition.

At the operation 1014, controlling the functionality of a computing device according to the aspect of the consumable composition may occur (e.g. a personal computer may prevent logging on unless an amount of a consumable composition has been calculated as ingested). For example, as shown in FIG. 1, control logic 122 may cause communications module 130 transmit control data (e.g., a decryption key) to a controllable device 185, such as a personal digital assistant (PDA), personal computer, laptop, and the like, according to the aspect of the consumable composition.

At the operation 1016, controlling the functionality of a communications device according to the aspect of the consumable composition may occur (e.g. a cell phone may prevent outgoing calls unless an amount of a consumable composition has been calculated as ingested). For example, as shown in FIG. 1, control logic 122 may cause communications module 130 transmit control data (e.g., subscriber identification data, a domain name, a communications frequency) to a controllable device 185, such as a cell phone, satellite phone, Blackberry®, land-line phone, and the like, according to the aspect of the consumable composition.

At the operation 1018, controlling the functionality of a gaming device according to the aspect of, the consumable composition may occur (e.g. a gaming system will not power on unless an amount of a consumable composition has been calculated as ingested). For example, as shown in FIG. 1, control logic 122 may cause communications module 130 transmit control data (e.g., power up codes) to a controllable device 185, such as gaming systems manufactured by Sony®, Microsoft®, Nintendo®, and the like, according to the aspect of the consumable composition.

At the operation 1020, controlling the functionality of a financial system according to the aspect of the consumable composition may occur (e.g. access to a banking network may be denied unless an amount of a consumable composition is calculated as ingested). For example, as shown in FIG. 1, control logic 122 may cause communications module 130 transmit control data (e.g., a system flag) to a controllable device 185, to prevent access (e.g. a login) to a financial system or prevent a system from completing transactions (e.g. ATM withdrawls) according to the aspect of the consumable composition.

Further, at the operation 1022, controlling the functionality of a credit system according to the aspect of the consumable composition may occur (e.g. a credit card may be disabled from making purchases unless an amount of a consumable composition has been calculated as ingested). For example, as shown in FIG. 1, control logic 122 may cause communications module 130 transmit control data to a controllable device 185, such as a monetary credit system (e.g. a credit card, online credit account) or a non-monetary credit system (e.g. an airline rewards program, a virtual credit account associated with a virtual environment such as an online gaming environment) and the like, according to the aspect of the consumable composition.

Further, at the operation 1024, the controlling the functionality of a banking system according to the aspect of the consumable composition may occur (e.g. a debit card may be disabled from making purchases unless an amount of a consumable composition has been calculated as ingested). For example, as shown in FIG. 1, control logic 122 may cause communications module 130 transmit control data to a controllable device 185, such as a bank debit card, an ATM, online bank account access, and the like, according to the aspect of the consumable composition.

FIG. 9 illustrates an operational flow 900 representing example operations related to programmed dispensing of consumable compositions. FIG. 9 illustrates an example embodiment where the example operational flow 200 of FIG. 2 may include at least one additional operation. Additional operations may include an operation 910.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system for administering a consumable composition, the method comprising:
    means for dispensing a dose of a consumable composition according to a programmed dosing schedule; and
    means for communicating an aspect of the consumable composition to a system associated with a monitoring entity.

2. The system of claim 1, wherein the means for communicating an aspect of the consumable composition to a system associated with a monitoring entity further comprises:
    means for calculating a difference between an amount of the consumable composition that is dispensed according to the programmed dosing schedule and an amount of the consumable composition that is calculated as ingested; and
    means for communicating the difference between an amount of the consumable composition that is dispensed according to the programmed dosing schedule and an amount of the consumable composition that is calculated as ingested to a monitoring entity.

3. The system of claim 1, wherein the means for communicating an aspect of the consumable composition to a system associated with a monitoring entity further comprises:
    means for communicating an amount of the consumable composition dispensed to a system associated with a monitoring entity.

4. The system of claim 3, wherein the means for communicating an amount of the consumable composition dispensed to a system associated with a monitoring entity further comprises:

means for communicating an amount of the consumable composition dispensed to a system associated with a consumable composition supply entity.

5. The system of claim 3, wherein the means for communicating an amount of the consumable composition dispensed to a system associated with a monitoring entity further comprises:
means for communicating an amount of the consumable composition dispensed to a system associated with a medical monitoring entity.

6. The system of claim 5, wherein the means for communicating an amount of the consumable composition dispensed to a system associated with a medical monitoring entity further comprises:
means for communicating an amount of the consumable composition dispensed to a system associated with a health care provider.

7. The system of claim 3, wherein the means for communicating an amount of the consumable composition dispensed to a system associated with a monitoring entity further comprises:
means for communicating an amount of the consumable composition dispensed to a system associated with an insurance entity.

8. The system of claim 7, wherein the means for communicating an amount of the consumable composition dispensed to a system associated with an insurance entity further comprises:
means for communicating an amount of the consumable composition dispensed to a system associated with an insurance entity in compliance with an insurance benefit program.

9. The system of claim 3, wherein the means for communicating an amount of the consumable composition dispensed to a system associated with a monitoring entity further comprises:
means for communicating an amount of the consumable composition dispensed to a system associated with a legal entity.

10. The system of claim 9, wherein the means for communicating an amount of the consumable composition dispensed to a system associated with a legal entity further comprises:
means for communicating an amount of the consumable composition dispensed to a system associated with a parole entity.

11. The system of claim 1, wherein the means for communicating an aspect of the consumable composition to a system associated with a monitoring entity further comprises:
means for communicating an amount of the consumable composition calculated as ingested to a system associated with a monitoring entity.

12. The system of claim 11, wherein the means for communicating an amount of the consumable composition calculated as ingested to a system associated with a monitoring entity further comprises:
means for communicating an amount of the consumable composition calculated as ingested to a system associated with a consumable composition supply entity.

13. The system of claim 11, wherein the means for communicating an amount of the consumable composition calculated as ingested to a system associated with a monitoring entity further comprises:
means for communicating an amount of the consumable composition calculated as ingested to a system associated with a medical monitoring entity.

14. The system of claim 13, wherein the means for communicating an amount of the consumable composition calculated as ingested to a system associated with a medical monitoring entity further comprises:
means for communicating an amount of the consumable composition calculated as ingested to a system associated with a health care provider.

15. The system of claim 11, wherein the means for communicating an amount of the consumable composition calculated as ingested to a system associated with a monitoring entity further comprises:
means for communicating an amount of the consumable composition calculated as ingested to a system associated with an insurance entity.

16. The method of claim 15, wherein the means for means for communicating an amount of the consumable composition calculated as ingested to a system associated with an insurance entity further comprises:
means for communicating an amount of the consumable composition calculated as ingested to a system associated with an insurance entity in compliance with an insurance benefit program.

17. The system of claim 11, wherein the means for communicating an amount of the consumable composition calculated as ingested to a system associated with a monitoring entity further comprises:
means for communicating an amount of the consumable composition calculated as ingested to a system associated with a legal entity.

18. The system of claim 17, wherein the means for communicating an amount of the consumable composition calculated as ingested to a system associated with a legal entity further comprises:
means for communicating an amount of the consumable composition calculated as ingested to a system associated with a parole entity.

19. The system of claim 1, wherein the means for communicating an aspect of the consumable composition to a system associated with a monitoring entity further comprises:
means for communicating a request to initiate a resupplying of the consumable composition.

20. The system of claim 1, wherein the means for communicating an aspect of the consumable composition to a system associated with a monitoring entity further comprises:
means for communicating an authorization to provide payment for a supply of the consumable composition.

21. The system of claim 1, wherein the means for communicating an aspect of the consumable composition to a system associated with a monitoring entity further comprises:
means for protecting a communicated aspect of the consumable composition by at least one of: associating a password with the communicated aspect of the consumable composition; associating a passcode with the communicated aspect of the consumable composition; and encrypting the communicated aspect of the consumable composition.

22. The system of claim 1, wherein the means for communicating an aspect of the consumable composition to a system associated with a monitoring entity further comprises:
means for communicating an aspect of the consumable composition to a system associated with a reward entity.

23. The system of claim 1, further comprising:
means for configuring a communication parameter according to a user input, the communications parameter including at least one of: a timing of a communication of an aspect of the consumable composition; a party to which a communication of an aspect of the consumable composition is to be directed; and a communication mechanism to be used to communicate an aspect of the consumable composition.

24. The system of claim 11, further comprising:

means for calculating an ingestion of an amount of the consumable composition including at least one of: a biometric sensor, an accelerometer, an inertial motion sensor, a pressure sensor, a capacitive concentration sensor, and an inclinometer.

\* \* \* \* \*

UNITED STATES PATENT AND TRADEMARK OFFICE
CERTIFICATE OF CORRECTION

PATENT NO. : 8,457,783 B2
APPLICATION NO. : 12/002794
DATED : June 4, 2013
INVENTOR(S) : Hyde et al.

Page 1 of 1

It is certified that error appears in the above-identified patent and that said Letters Patent is hereby corrected as shown below:

In the Claims

Column 14, Line 39 should read:

--the ~~method~~system comprising:--

Signed and Sealed this
Eighth Day of July, 2014

Michelle K. Lee
*Deputy Director of the United States Patent and Trademark Office*